United States Patent [19]

Lee

[11] 4,214,598

[45] Jul. 29, 1980

[54] DENTAL FLOSS APPLICATOR

[76] Inventor: Lawrence L. Lee, c/o Dr. C. J. Gerritsma, N.V. Philips' Gloeilampenfabrieken Research Laboratory, Eindhoven, Netherlands

[21] Appl. No.: 951,190

[22] Filed: Oct. 13, 1978

[51] Int. Cl.³ .............................................. A61C 15/00
[52] U.S. Cl. .................................................. 132/92 R
[58] Field of Search ....................... 132/92 A, 91, 92 R

[56] References Cited

U.S. PATENT DOCUMENTS

| | | | |
|---|---|---|---|
| 1,210,207 | 12/1916 | Roach | 132/92 R |
| 2,450,635 | 10/1948 | Dembenski | 132/92 A |
| 3,734,107 | 5/1973 | Thierman | 132/92 A |
| 3,861,406 | 1/1975 | Stitt | 132/92 A |
| 4,031,908 | 6/1977 | Ting | 132/91 |

*Primary Examiner*—G. E. McNeill
*Attorney, Agent, or Firm*—Gust, Irish, Jeffers & Hoffman

[57] ABSTRACT

A dental floss applicator for use in dispensing and supporting a strand of dental floss under tension for cleaning the teeth comprises an elongated supporting frame having on one end two spaced furcations laterally extending therefrom. Tips on the furcations are provided with floss-guiding portions by means of which a floss strand may be tensioned therebetween. A capstan device is frictionally mounted for rotation on said frame and further is provided with supply and take-up capstan portions axially spaced apart. A supply of floss strand is carried by the frame. The take-up capstan portion is of slightly larger circumference than is the supply capstan portion. Means are provided for guiding the floss strand from the supply, around the supply capstan portion in one circumferential direction when viewing the latter capstan directly, to and between said floss-guiding portions on the furcations, back to and around the take-up portion in the opposite circumferential direction when viewing the latter capstan directly, whereby rotation of the capstan device in a direction to withdraw floss strand from the supply causes advancement of the floss between said floss-guiding portions, the difference in circumference of the supply and take-up capstan portions tensioning the floss strand between said tips.

15 Claims, 10 Drawing Figures

U.S. Patent  Jul. 29, 1980  4,214,598
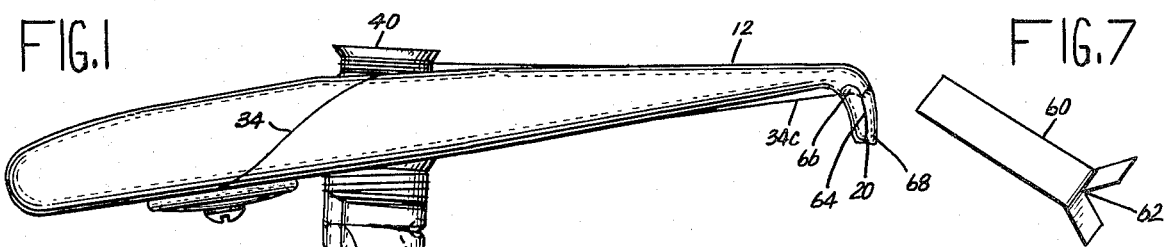
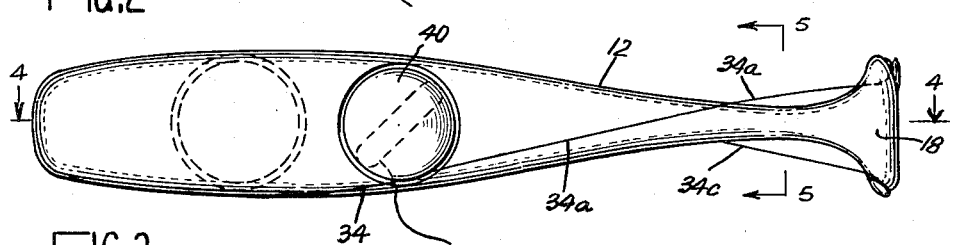
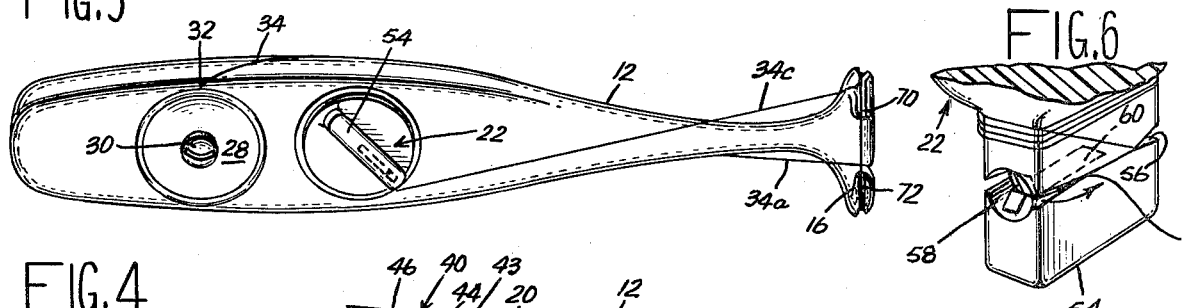
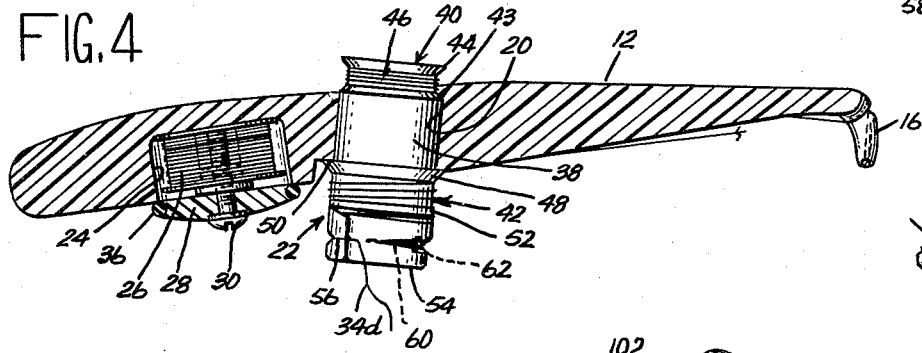
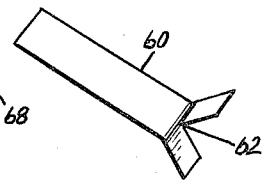
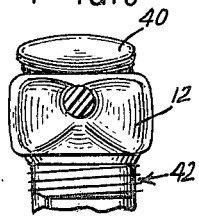
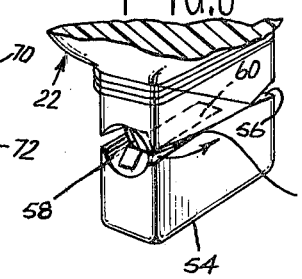
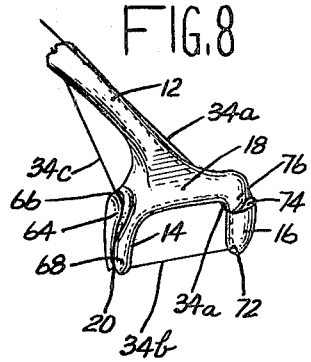
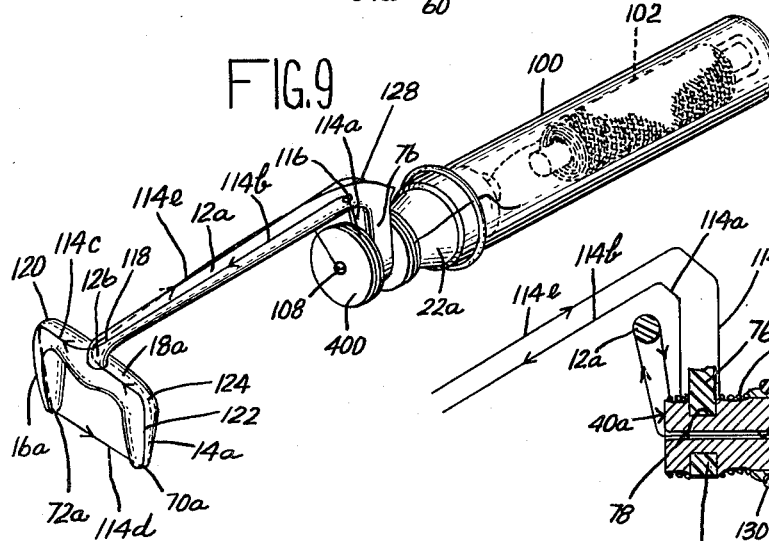
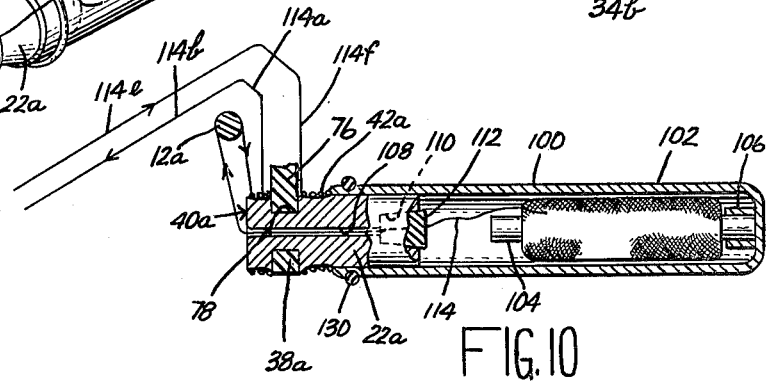

DENTAL FLOSS APPLICATOR

BACKGROUND OF THE INVENTION

1. Field of the Invention

The present invention relates to dental floss applicators for use in dispensing and supporting a strand of dental floss under tension for cleaning the teeth, and more particularly to an applicator capable of facile manipulation to advance a new segment of dental floss into useable position while simultaneously generating and holding necessary tension.

2. Description of the Prior Art

Dental floss applicators serving the general purpose of this invention are disclosed in prior art patents including U.S. Pat. Nos. 1,582,000; 2,577,597; 3,759,273; 3,814,114; 3,847,168; 3,903,907; 3,908,677; 3,992,085; 4,005,722 and 4,008,728. Generally, such applicators include a frame having furcations between the ends of which dental floss is maintained in tension. Supply and take-up spools on the frame accompanied by floss-guiding structure permit segments of worn floss between the furcations to be replaced as required by manipulating the supply and takeup spools. In order to maintain tension, it is customary to provide jamming or locking devices engageable with the strand to hold the floss tension. When it is desired to advance the floss, it is necessary to remove the lock before such advancement may occur. In some applicators, it is necessary for the floss to be threaded through holes in the applicator which is not easily accomplished and certainly reduces convenience in utilizing the applicator. In still others, advancement of the floss is performed manually and once the proper tension has been achieved, the floss is locked into position by another manipulation.

SUMMARY OF THE INVENTION

The present invention constitutes an improvement over the prior art in the respect that a single capstan device may be manipulated for achieving simultaneously the different functions of floss advancement, generation of floss tension and the holding of such tension once generated. Generally, the dental floss applicator of this invention is for use in dispensing and supporting a strand of dental floss under tension for cleaning the teeth. It includes an elongated supporting frame having on one end two spaced furcations which laterally extend therefrom. Tips on the furcations are provided with floss-guiding portions by means of which a floss strand may be tensioned therebetween. A unitary capstan device is frictionally mounted for rotation on the frame and is provided with supply and take-up capstan portions axially spaced apart. A supply of dental floss strand is carried within the frame. The take-up capstan portion is of larger circumference than the supply capstan portion. Means are provided for guiding the floss strand from the source of supply, around the supply capstan portion in one circumferential direction when viewing the latter portion directly, to and between the floss-guiding portion, back to and around the take-up portion in the opposite circumferential direction when viewing the latter portion directly, whereby rotation of the capstan device in a direction to withdraw floss from the supply causes advancement of floss between the floss-guiding portions, the difference in circumference between the supply and take-up capstan portions tensioning the floss strand between the floss-guiding portions. Since the strand is under tension and is wrapped around the supply and take-up capstan portions in opposite directions, opposite torques are applied to the capstan device. By proper selection of the circumferences of the supply and take-up portions and the degree of friction employed in the mounting of the capstan device on the frame, the torques are substantially equal and opposite such that when coupled with the frictional resistance causes no rotation of the capstan device thereby retaining the floss strand in tension.

OBJECTS OF THE INVENTION

It is therefore an object of this invention to provide a dental floss applicator capable of facile replenishment of the working strand of floss controlled by the simple manipulation of a single capstan device.

It is another object of this invention to provide a dental floss applicator wherein the manipulation of a single capstan device serves the purpose of floss advancement, generating desired tension in the floss and holding this tension without any further manipulations being required.

The above-mentioned and other features and objects of this invention and the manner of attaining them will become more apparent and the invention itself will be best understood by reference to the following description of an embodiment of the invention taken in conjunction with the accompanying drawings.

BRIEF DESCRIPTION OF THE DRAWINGS

FIG. 1 is a side view of a preferred embodiment of this invention;

FIG. 2 is a bottom plan view thereof;

FIG. 3 is a top plan view slightly in perspective;

FIG. 4 is a longitudinal sectional view;

FIG. 5 is a cross section taken substantially along section line 5—5 of FIG. 2;

FIG. 6 is an enlarged fragmentary view of the floss cutoff device carried by the capstan;

FIG. 7 is an edge view of the cut-off plate employed in the cut-off device of FIG. 6;

FIG. 8 is a view in perspective of the end portion of the applicator;

FIG. 9 is a perspective view of a second embodiment of this invention; and

FIG. 10 is a longitudinal sectional view of the embodiment of FIG. 9 with the dental floss arrangement partially diagrammed.

DESCRIPTION OF THE PREFERRED EMBODIMENT

Referring to the drawings, the applicator comprises an elongated, rigid body 12 formed of a suitable plastic material such as high density polyethylene. It is shaped as shown, being provided with rounded corners and edges on all parts so as to avoid chafing of the dental floss and to facilitate manipulation. Molded integrally onto one end of the body 12 are furcations 14 and 16 generally parallel and spaced apart extending laterally from the body 12. The adjacent portion of the body 12 is necked down as shown and widens at the end to provide a bridge portion 18 from which the furcations 14 and 16 extend. As before, all corners and edges are rounded.

About midway between the ends, the body 12 is provided with a cylindrical bearing opening 20 which frictionally receives for rotation a capstan device indicated generally by the numeral 22. To the left side of the capstan device 22 as viewed in FIGS. 1 through 4, the body 12 is provided with a cylindrical cavity 24 which receives a spool of floss strand 26. A small plastic cap 28 is secured to the body 12 over the opening of cavity 24 by means of a threaded fastener 30 thereby to retain the spool of floss 26 in place.

The cavity 24 is suitably sealed by means of an O-ring 36 of rubber or the like mounted on the perimeter of the cover 28, this O-ring also serving to apply a slight friction to the floss.

The capstan device 22 is a one-piece structure preferably integrally molded or composed of assembled parts as will be apparent from the description that follows. It should be made of material hard enough to withstand the compression of the floss under tension. Delrin (Dupont trademark for Acetal plastic) is an appropriate material; metals and other hard plastics can also be used. Between the end portions, the capstan device 22 is provided with a journal bearing portion 38 which frictionally fits into the bearing opening 20. On one end is a supply capstan portion 40 and on the other end a take-up capstan portion 42. It will be noted that both portions 40 and 42 project beyond the adjacent sides of the body 12.

For a purpose to be explained later, the axis of the capstan device 22 is canted slightly with respect to the longitudinal axis of the body 12. The supply capstan 40 is of a diameter no larger than the journal bearing 38 so that the capstan device 22 may be easily inserted into the bearing opening 20 and removed as may be desired.

The portion 40 is composed of two flanges 43 and 44 and a cylindrical barrel section 46. The flanges 43 and 44 are tapered inwardly to the barrel section 46 as shown. It will be noted that the side of supply portion 40 toward the right is slightly recessed within the bearing opening 20 while the opposite portion thereof protrudes just beyond the side of body 12.

The take-up capstan portion 42 also is provided with an annular flange 48 of a size larger than the bearing opening 20 to engage the flat surface 50 on the body 12 surrounding the opening 20. This annular flange 48 serves to locate the capstan device 22 in the bearing opening 20 and to prevent the floss from entering the bearing area.

The annular flange 48 is tapered as shown to merge with a second barrel section 52 on the take-up portion, a rectangular knob 54 projecting axially beyond the barrel section 52.

As shown more clearly in FIG. 6, the knob 54 has two slots 56 and 58 formed into opposite edges thereof, both being generally V-shaped, one being used for holding the end of the floss. The slot 58 is V-shaped and enlarged somewhat to receive a cut-off plate 60 (FIG. 7) having one end lanced and bifurcated at 62 in registry with the open slot 58. With the plate 60 firmly mounted in place, a strand of dental floss inserted into the slot 58 will engage the furcation 62 which is provided with sharp enough edges to cut through the floss.

Referring more particularly to FIGS. 2, 3 and 8, the furcations 14 and 16 are provided with grooves which receive the floss strand. Referring to the furcation 14, the groove is indicated by the numeral 64 and extends over the radius 66 at the base thereof and longitudinally along the outer edge to the tip 68 having a communicating groove 70 in the tip thereof.

The furcation 16 has a like groove 72 in the tip thereof, the two grooves 70 and 72 being in straight line alignment, and from the groove 72 longitudinally along the outer edge to the groove portion 74 around the butt portion 76 thereof.

The pattern of threading the floss on the applicator will now be described. The floss strand 34 (FIG. 3) is withdrawn from the spool 28 around the body 12 where it is wrapped about three turns around the barrel section 46 (FIGS. 2 and 4) counterclockwise as shown in FIG. 2. From the barrel 46, this strand extends as indicated by the numeral 34a along the body 12 to the furcation 16, the strand 34a passing on the inside of the furcation 16 around and through the groove 76 (FIG. 8) through the groove 74, the groove 72 and across the span to the furcation 14. Here the strand portion indicated by the numeral 34b passes through the grooves 70 and 64 over the outside of the butt portion 66 to a position indicated by the numeral 34c. The section 34c then extends to and wraps around the barrel section 52 of the take-up capstan portion 42 clockwise, two or more turns, the end then being forced into the groove 56 which retains the strand indicated by numeral 34d in FIG. 4 in place. It should be noted at this point that the strand 34 is shown wrapped around the two capstan portions 40 and 42 in opposite directions with respect to the frame.

The floss is normally wrapped around the supply capstan 40 counterclockwise (see FIG. 2) and around the take-up capstan 42 (see FIG. 3) clockwise; therefore it is indeed wrapped in opposite directions. Consequently, as the floss is advanced, viewing the application in the position of FIG. 3, by turning the knob 54, the floss travels clockwise around both the supply and take-up capstans.

Upon clockwise rotation of the capstan 22 as viewed in FIG. 3 so as to wrap more strand onto the take-up portion 42, the strand will be drawn through the various grooves, unwinding from capstan supply portion 40, strand from the supply spool 26 simultaneously being wound onto the supply portion 40. The various parts of the applicator described thus far are so sized that about one-half revolution of the capstan device 22 will move the strand a length equal to the space between the two furcations 14 and 16.

An important feature of this invention resides in the fact that the take-up capstan portion 42 is slightly larger in diameter and circumference than the supply capstan portion 40. Upon rotationally adjusting the capstan device 22 clockwise, the floss is thereby tensioned.

Turning the capstans a small angle $\theta$ radians, a length $\theta r_2$ of stretched floss is drawn onto the take-up capstan and a length of $\theta r_1$ of unstretched floss is drawn onto the supply capstan. But, the floss becomes stretched passing around the supply capstan, so every length $\theta r_1$ of unstretched floss passing onto the supply capstan becomes $\theta r_1(1+T/k)$ long as it passes off. ("T" is tension, "k" the elastic modulus). The floss between capstans is stretched by $\downarrow r_2 - \theta r_1(1+T/k)$, therefore its tension increases by $k/x[\theta r_2 - \theta r_1(1+T/k)]$ where "x" is the length of the floss between capstans. Initially, when T is zero, the rate of increase is maximum, being $k/x(r_2-r_1)$ per radian: as T increases, its rate of increase decreases. T reaches a limit of $$k(r_2-r_1/r_1)$$

from that value, there will be no further increase. This analysis is by no means exact as it ignores the nonuniformity of tensions at different positions. However, it suffices for the purpose of explaining this invention.

Since the floss is wrapped around the capstan portions 40 and 42 in opposite directions, and since the floss is tensioned, torque is applied to both capstan portions in opposite directions. More particularly, the floss exerts a torque "$L_1$" on the capstan device 22 equal to the tension "T" times the difference in radii of portions 46 and 52, or in other words, $$L_1 = T(r_2 - r_1).$$

This torque is typically small, because the radii of the two capstan barrels 46 and 52 are almost equal. Typical radii are 0.75 inches for the barrel section 46 and 0.79 inches for the barrel section 52.

The frictional resistance against rotation of the capstan 22 in the bearing opening 20 must exceed this torque "$L_1$" in order to prevent slippage. The torque required to turn the capstan is, therefore, $L_1$ plus the frictional force, again typically small and in most cases made to be less than $2r_1T$, which would be the minimum torque needed for manually rotating the capstan of a single-capstan device.

In the operation of the applicator, the capstan 22 is rotated until the floss across the furcations 14 and 16 is suitably tensioned. The floss is then used in the typical manner by inserting the section 34b between the teeth. The user can bite down on the end portion of the body, and more particularly the bridge portion 18, to force the floss section 34b between teeth that are closely spaced. By controlling the length of the furcations 14 and 16, the floss portion 34b can be kept from entering too deeply into the gingiva even in case of misuse since the under portion of the bridge 18 will urge the incisal edge of the teeth thereby preventing deep penetration.

Once the section 34b becomes worn, the capstan 22 is rotated about one-half turn, or in other words, sufficiently to span the furcations 14 and 16 with a new section of floss. For this adjusted position, the floss will have about the same tension as before, and no further manipulations need to be performed in order to maintain this tension, the opposed torque on the two capstan portions 40 and 42 plus the frictional fit of the journal bearing 38 in the opening 20 preventing the capstan 22 from slipping or turning.

Should the floss become too highly tensioned, such tension can be reduced simply by slightly turning the capstan 22 in reverse by an amount necessary to obtain the desired tension.

Referring to the second embodiment of this invention shown in FIGS. 9 and 10, like parts are indicated by the same numerals with the suffix letter "a" added. The elongated slender body 12a carries on the distal end the two furcations 14a and 16a. On the opposite end, a supporting arm 76 extends at right angles and is furcated to provide a bearing notch 78 (FIG. 10). The capstan device 22a has a journal portion 38a which frictionally fits into the furcation 78. The journal 38a is of reduced diameter defining a groove which axially separates the supply capstan portion 40a and the take-up capstan portion 42a. The groove defined by the journal 38a is of a width which frictionally but rotationally embraces the arms 76 for providing the desired degree of friction described hereinbefore.

The capstan device 22a is removably secured into the end of a hollow handle 100 coaxially extending therefrom. The securement between the capstan 28a and the handle 100 is preferably in the form of a friction fit which provides against the leakage of water. Mounted inside the handle 100 is a supply 102 of dental floss.

The capstan device 22a is provided with a coaxial bore 108 which is enlarged at 110 in its right hand end to receive a rubber stopper 112 having a passage coaxially therethrough which slidably receives a strand of floss 114 payed off the spool 102. The strand 114 also threads through the bore 108 and from there extends radially outwardly about the body 12a and back onto supply capstan 40a where it is wrapped in one direction three turns therearound. Alternatively, the body 12a may be provided with a transverse aperture (not shown) through which the strand 114 is threaded for its return to the supply capstan 40a.

From the supply capstan 40a, the strand 114, as indicated by the numeral 114a is threaded through an opening 116 (or hook) on the body 12a disposed radially opposite the central portion of supply capstand 40a. From the opening 116, the strand indicated by the numeral 114b extends along the length of the body 12a where it fits into a slot 118 at the distal end curved to accomodate the strand section 114c to extend transversely and over the outer longitudinal edge of the furcation 16a. The furcation 16a is slotted from its butt portion 120 along its longitudinal extent to the tip slot 72a for receiving the strand portion 114c.

The strand segment 114d extends from the slot 72a through the slot 70a in the tip of furcation 14a, upwardly through the longitudinal slot 122 in the outer longitudinal edge thereof around the butt 124 along the bridge portion 18a where it enters a slot 126 in the distal end of the body 12a curved to direct the strand segment indicated by the numeral 114e longitudinally along the top side of the body 12a. At the rear end of the body 12a, the top side is radiused where it joins to the arm 76, being provided with a smoothly rounded slot 128 therein which guides strand segment 114f onto the radially opposite take-up capstan 42a. Here the strand 114f is wrapped around capstan 42a a few turns in a direction opposite to that on the supply capstan 40a. The end of the strand is then slipped beneath a rubber O-ring fitted tightly around the handle 104 which serves to hold the strand end in place.

As in the first embodiment, the take-up capstan 42a is of slightly larger circumference than the supply capstan 40a.

In operation, after the floss strand has been threaded as described, the handle 100 is rotated, while holding the body 12a stationary, in a direction to wrap more strand 114f therearound. This results in floss being payed off the supply capstan 40a and movement of the floss segment 114d across the space between the two furcations 14a and 16a. As the capstan 22a is rotated with the handle 100, floss from the supply 102 is drawn through the stopper 112 and bore 108 around the body 12a and onto the supply capstan 40a. When a new section 114b of floss spans the furcations 14a and 16a, the rotation is stopped as before.

It is well to mention at this point that the purpose of the stopper 112 is to provide a seal against liquid flowing through the bore 108 back into the interior of the handle 100 and to apply a slight friction to the floss.

As before, during rotation of the handle 100, the strand is tensioned and this tension is maintained by reason of the substantially equal and opposite torques exerted on the supply and take-up capstan portions 40a and 42a. The frictional fit between the journal 38a and the bearing portion 78 is sufficient to overcome the slight difference that may exist in the two torques such that the capstan 22a will not rotate in reverse.

With respect to both embodiments, a complete change of exposed floss between the furcations 14a and 16a is obtained by means of rotating the capstan device 22, 22a a needed amount, and in a working embodiment being about one-half revolution. In threading the floss through the instrument, it is not necessary to tie any knots therein to hold the floss in place, nor in the first embodiment to thread the floss through any holes which is a tedious operation. By reason of the different diameters in the supply and take-up capstans, advancement of the floss across the furcations is accompanied by tensioning. Replenishment of the working segment of floss is thus accompanied simultaneously by the suitable tensioning thereof. Again, if at any time it should be desired to reduce the tension, it is only necessary to turn the capstan device 22, 22a a partial revolution in reverse. This results in floss paying off the take-up capstan portion without any accumulation on the supply capstan portion, assuming of course that the reversal is only sufficient to relieve tension.

With respect to the first embodiment of FIGS. 1 through 8, the slight canting of the capstan device prevents overlapping of the floss turns about the supply and take-up portions 40, 42 such that the floss is not resisted in its advancement to, about and from the supply capstan portion 40. Furthermore, when it becomes necessary to remove any excess floss accumulated on the take-up capstan, it may easily be stripped by sliding it axially thereoff.

The working end of the instrument composed essentially of the furcations 14a and 16a is designed to provide maximum strength. To this end, they are relatively short and stubby compared with like structures in the prior art, serving the purpose of preventing the floss from entering too deeply the interdental spaces to a point at which the gingiva might be seriously injured. The shape of the working head (14, 16, 18) permits biting down to force the floss between the teeth.

The capstan device 22, 22a being in one piece facilitates its removal, cleaning and replacement. While the capstan device preferably is integrally formed, it obviously may be composed of a plurality of parts which when assembled has the configuration shown and described.

Of salutary importance is the fact that by means of a single capstan device 22, 22a the floss is (1) advanced, (2) tensioned and (3) the tension maintained without requiring any manipulation other than the advancement. No additional elements or devices are required for tensioning or locking the floss against loss of tension.

While there have been described above the principles of this invention in connection with specific apparatus, it is to be clearly understood that this description is made only by way of example and not as a limitation to the scope of the invention.

What is claimed is:

1. A dental floss applicator for use in dispensing and supporting a strand of dental floss under tension for cleaning the teeth comprising an elongated supporting frame having on one end two spaced furcations laterally extending therefrom, tips on said furcations having floss-guiding portions by means of which a floss strand may be tensioned therebetween, a capstan device mounted for rotation on said frame with supply and takeup capstan portions axially spaced thereon and a common support, floss on said frame, said take-up capstan portion being of larger circumference than said supply capstan portion, a supply of floss carried by said frame and means for guiding floss therefrom to said supply capstan portion, means for guiding said floss around said supply capstan portion in one circumferential direction when viewing said take-up capstan portion directly to and between said floss-guiding portions, back to and around said take-up portion in the opposite circumferential direction when viewing said takeup capstan portion directly, whereby rotation of said capstan device in a direction to wind floss onto said supply capstan portion causes advancement of floss between said floss-guiding portions, the difference in circumference of the supply and take-up capstan portions tensioning the floss strand between said floss-guiding portions and maintaining such tension substantially constant upon successive adjusting advancements of said floss while providing for opposed torques on said supply and take-up capstan portions which are substantially equal.

2. The applicator of claim 1 wherein said capstan device is transaxially mounted on said frame.

3. The applicator of claim 2 wherein said capstan device is mounted with its axis at an angle other than ninety degrees with respect to the axis of said frame such that said supply portion is canted closer to said furcations than is said take-up portion.

4. The applicator of claim 3 wherein said frame is a body of plastic material with said furcations integral therewith, said capstan device being frictionally journalled in a bearing opening through said body, the axis of said bearing opening extending laterally in generally the same direction on said furcations, and the supply and take-up capstan portions being exposed beyond the respective sides of said body.

5. The applicator of claim 4 wherein said guiding means include slots extending longitudinally of said furcations in the outer portions thereof and said floss-guiding portions are also aligned slots communicating therewith, said floss strand extending from said supply capstan portion to and partially around a first furcation to fit into the slots thereof, across the space between said tips and into the slots of the second furcation and then back to said take-up capstan portion whereby rotation of said capstan device moves said floss strand through said slots between said tips.

6. The applicator of claim 5 wherein said supply of floss is carried in a cavity in the side of said body opposite from said supply capstan portion, the floss strand extending from said cavity over the edge of said body to wrap around said supply capstan portion.

7. The applicator of claim 6 wherein the portion of said body progressively decreases in cross-section from the region of said capstan device to said furcations, said furcations upstanding from the ends of an elongated bridge portion on said body and being substantially parallel, said furcations being rounded in crosssection thereby providing no sharp corners against which said floss strand may engage.

8. The applicator of claim 1 wherein said frame is a body of plastic material with said furcations integral therewith, said capstan device being frictionally journalled in a bearing opening through said body, the axis of said bearing opening extending laterally in generally the same direction on said furcations, and the supply and take-up capstan portions being exposed beyond the respective sides of said body, said capstan device being a one-piece structure having a cylindrical bearing journal between said take-up and supply portions; said supply portion being of a diameter no larger than said bearing journal and having axially spaced flanges on the opposed ends, respectively, of a barrel section, the facing surfaces of said flanges being included to form with said barrel section a generally v-shaped cross-section; said take-up capstan portion having an annular flange larger than said bearing journal engageable with a side portion of said body surrounding said bearing opening, said annular flange having a surface angled outwardly away from said body, said take-up portion further having a cylindrical shaped barrel section extending outwardly from said annular flange; said bearing journal rotatably frictionally fitting into said bearing opening, the degree of friction resisting rotation of said capstan device when said floss strand is tensioned between said furcations.

9. The applicator of claim 8 including a floss cut-off device on said take-up portion, said cut-off device including a radial slot for frictionally receiving and holding said floss strand, a metallic blade disposed in said radial slot and having a cutting edge protruding thereinto which cuts through the floss strand when it is forced into said radial slot.

10. The applicator of claim 1 wherein said capstan device is mounted with its axis generally parallel to the axis of said frame.

11. The applicator of claim 10 wherein said capstan device has a cylindrical bearing journal between said supply and take-up portions, said bearing journal being frictionally rotatably mounted in a bearing receptacle in said frame, the degree of friction preventing reverse rotation of said capstan device due to the tension on the floss.

12. The applicator of claim 11 wherein said frame is a body of plastic material with said bearing receptacle being on an arm laterally projecting from the end thereof opposite said furcations, said supply capstan portion being disposed on the side of said arm toward said furcations; said guiding means including a floss strand-receiving bore axially extending through said capstan device, an elongated hollow handle secured to said capstan device and containing a supply of floss strand, said strand extending from said supply through said bore and about a guide on said body back on to said supply capstan portion, about a first guide portion on said body to said floss-guiding portions, back to another second guide portion on said body and then to said takeup capstan portion.

13. The applicator of claim 12 wherein said guiding means further includes slots extending longitudinally of said furcations in the outer portions thereof and said floss-guiding portions are also aligned slots communicating therewith, said strand fitting into said slots.

14. The applicator of claim 13 wherein said first guide portion includes a curved passage in said body disposed radially opposite said supply capstan portion, said second guide portion includes a depression in said body radially opposite said takeup capstan portion, and a sealing plug in the supply end of said capstan bore having a passage therethrough which frictionally receives said floss strand.

15. The applicator of claim 1 wherein said capstan device is frictionally mounted for rotation on said frame, the torque on the supply and take-up capstan portions, when the floss strand between said tips is tensioned being less than required to rotate said capstan device against its frictional mounting in said frame.

* * * * *

UNITED STATES PATENT AND TRADEMARK OFFICE
CERTIFICATE OF CORRECTION

PATENT NO. : 4,214,598
DATED : July 29, 1980
INVENTOR(S) : Lawrence L. Lee

It is certified that error appears in the above-identified patent and that said Letters Patent are hereby corrected as shown below:

Column 4, line 56, the arrow should be changed to -- $\theta$ --.

Column 4, line 63, the formula should be changed to read:

$$-- k \left( \frac{r_2 - r_1}{r_1} \right) --$$

Signed and Sealed this

Ninth Day of December 1980

[SEAL]

Attest:

Attesting Officer

SIDNEY A. DIAMOND

Commissioner of Patents and Trademarks